United States Patent
Eichenseer

(10) Patent No.: US 7,404,674 B2
(45) Date of Patent: Jul. 29, 2008

(54) COMPUTED TOMOGRAPHY APPARATUS AND PATIENT POSITIONING TABLE THEREFOR ALLOWING ROTATION OF THE PATIENT SUPPORT PLATE

(75) Inventor: Mario Eichenseer, Pinzberg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/491,268

(22) Filed: Jul. 21, 2006

(65) Prior Publication Data
US 2007/0025527 A1    Feb. 1, 2007

(30) Foreign Application Priority Data
Jul. 21, 2005    (DE) ................. 10 2005 034 159

(51) Int. Cl.
*A61B 6/04* (2006.01)
(52) U.S. Cl. .......................... 378/209; 5/601
(58) Field of Classification Search ............. 378/20, 378/208–209; 5/600–601; 600/415
See application file for complete search history.

(56) References Cited

U.S. PATENT DOCUMENTS

| | | | |
|---|---|---|---|
| 5,013,018 A | 5/1991 | Sicek et al. | |
| 6,094,760 A | 8/2000 | Nonaka | |
| 6,198,789 B1 * | 3/2001 | Dafni | 378/8 |
| 6,955,464 B1 * | 10/2005 | Tybinkowski et al. | 378/209 |
| 6,986,179 B2 | 1/2006 | Varadharajulu et al. | |
| 7,008,105 B2 | 3/2006 | Amann et al. | |
| 2002/0028992 A1 * | 3/2002 | Dutto et al. | 600/415 |
| 2005/0129181 A1 | 6/2005 | Shinoda | |

* cited by examiner

*Primary Examiner*—Hoon Song
(74) *Attorney, Agent, or Firm*—Schiff Hardin LLP

(57) ABSTRACT

A patient positioning table has a base part with a longitudinal axis and a support plate for positioning a patient. The support plate can be displaced in the direction of the longitudinal axis of the base part relative to the base part. The support plate is provided with a device that can interact with an acceptance device of the base part such that the support plate can be rotated relative to the base part after acceptance of the device of the support plate into the acceptance device of the base part of the support plate. The patient positioning table is suitable for a computed tomography apparatus.

22 Claims, 4 Drawing Sheets

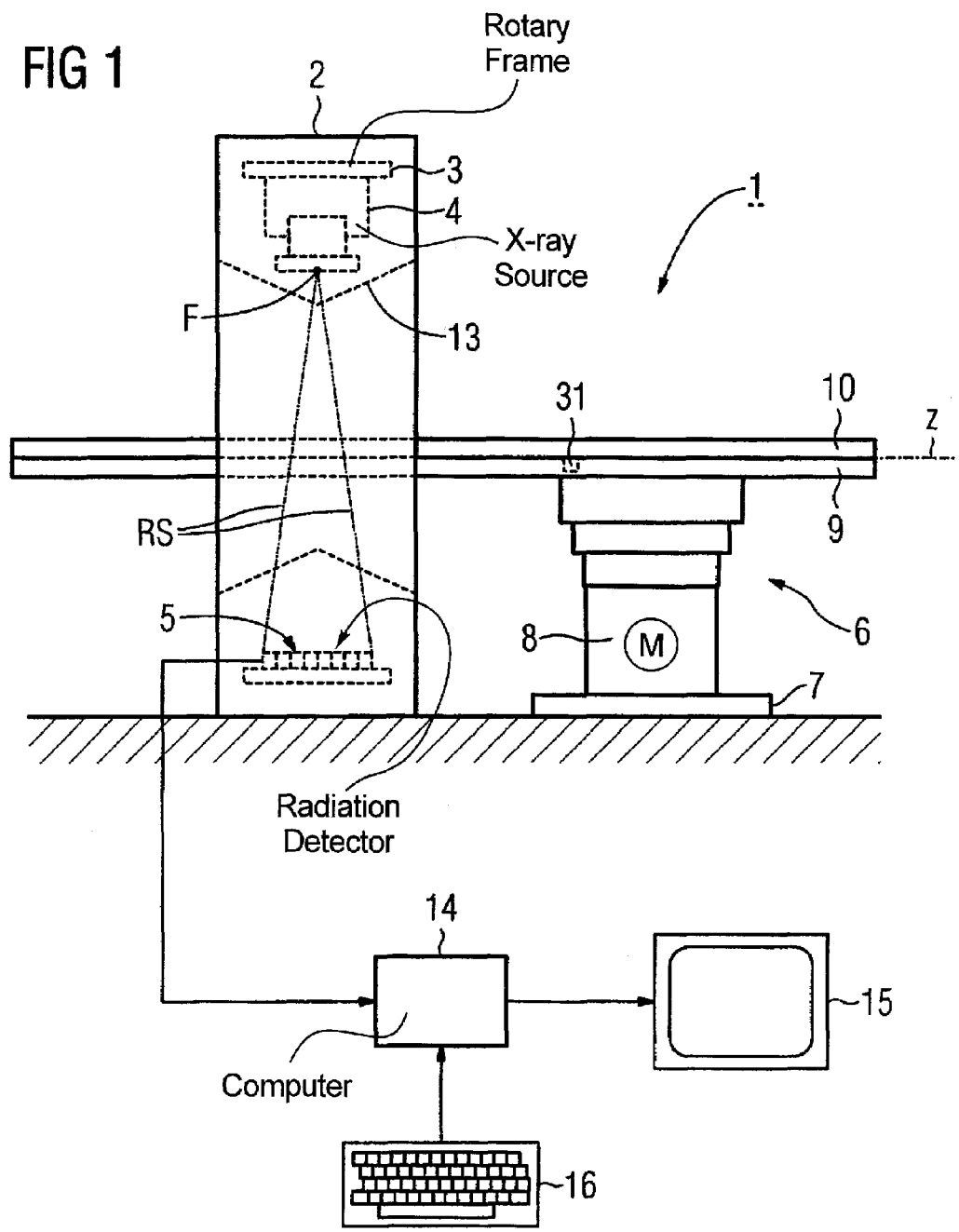

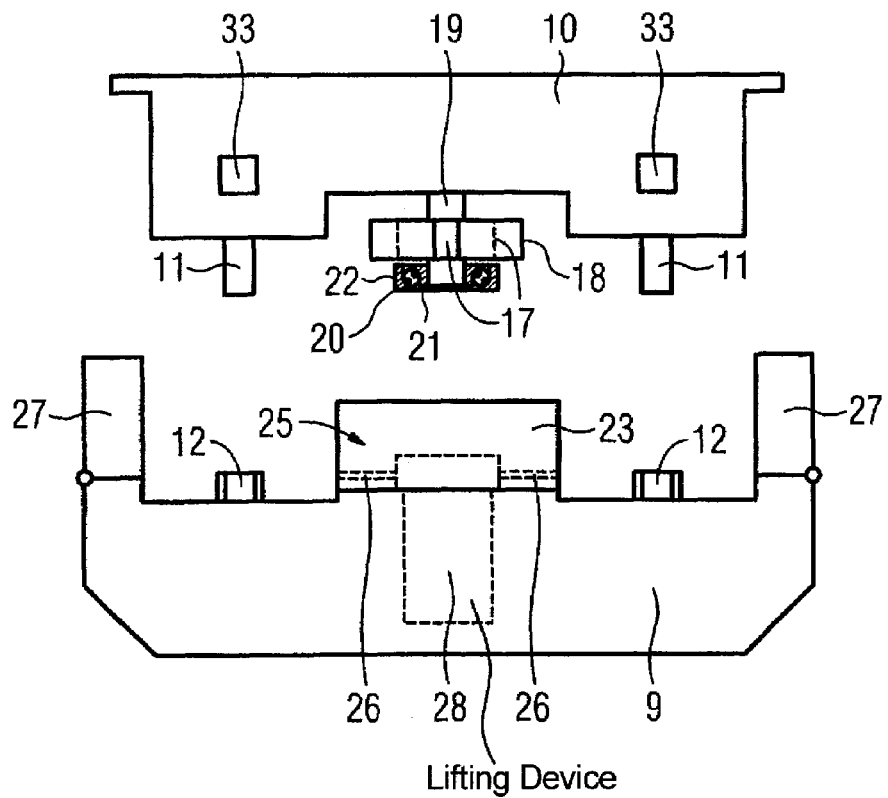
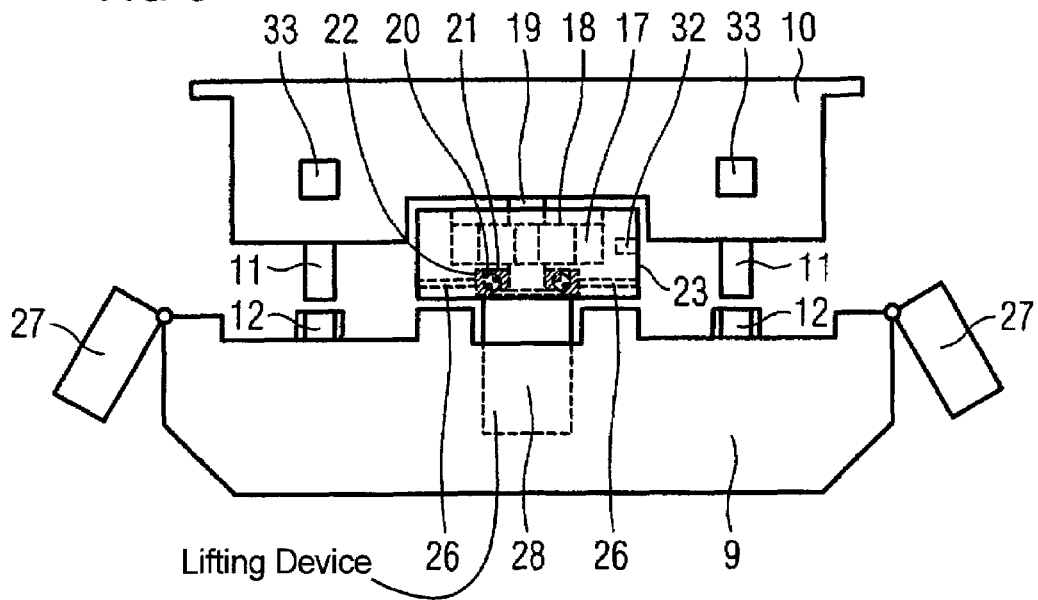

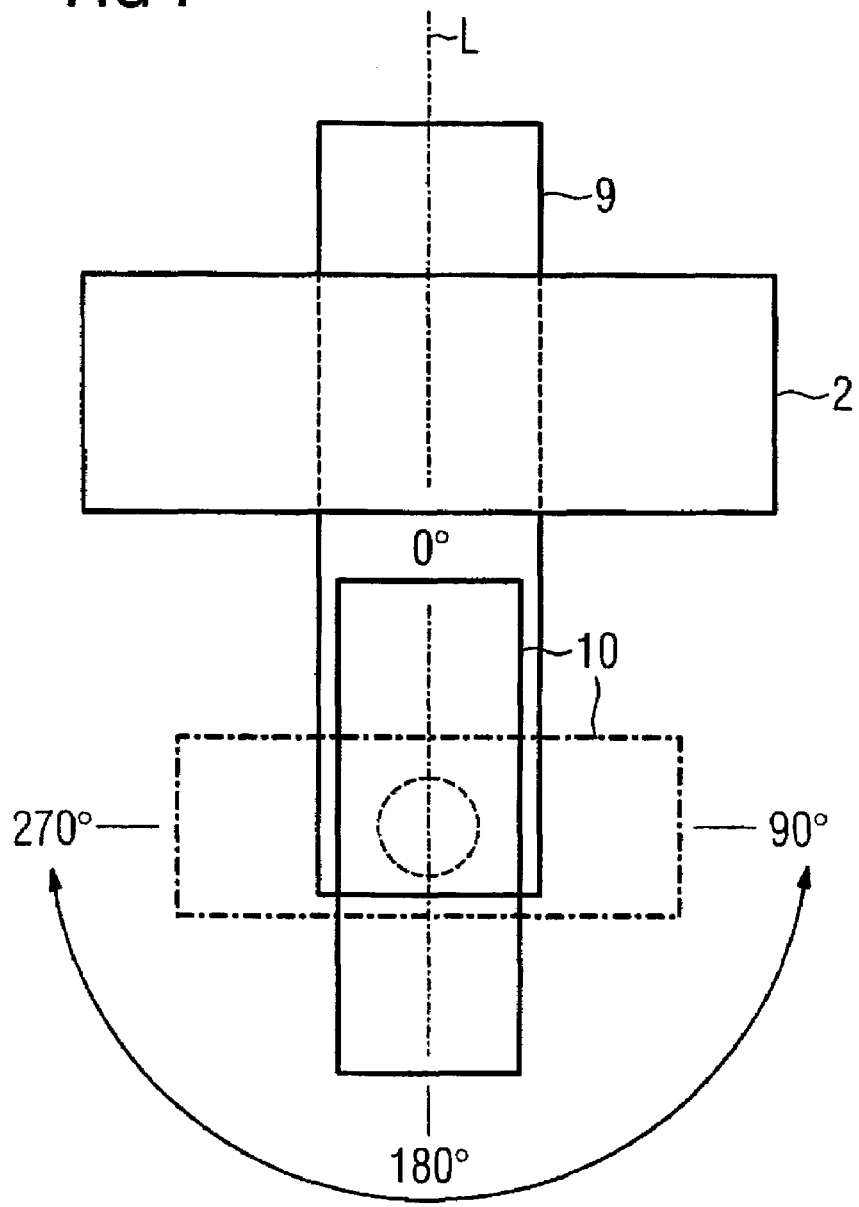

COMPUTED TOMOGRAPHY APPARATUS AND PATIENT POSITIONING TABLE THEREFOR ALLOWING ROTATION OF THE PATIENT SUPPORT PLATE

BACKGROUND OF THE INVENTION

1. Field of the Invention

The present invention concerns a patient positioning table of the type having a base part having a longitudinal axis and a support plate for supporting a patient, the support plate being displaceable in the direction of the longitudinal axis of the base part relative to the base part. The invention also concerns a computed tomography apparatus having such a patient positioning table.

2. Description of the Prior Art

For tomographic examination of a patient with a tomography apparatus, such as a magnetic resonance apparatus, a C-arm x-ray apparatus or (as described in detail in the following) an x-ray computed tomography apparatus, a patient is positioned on a support plate of a patient positioning table, the support plate normally being displaced relative to a measurement system of the tomography apparatus. For example, if a computed tomography apparatus is considered, the support plate of the patient positioning table can be displaced in the longitudinal direction through an opening of the gantry of the computed tomography apparatus. The radiological measurement system (formed by an x-ray source and an x-ray detector situated opposite thereto) is contained in the gantry.

If a patient who is not able to position himself or herself on the support plate (for example due to an injury or a physical limitation) is to be relocated from a bed aligned parallel to the patient positioning table onto the support plate of the patient positioning table, it frequently proves to be disadvantageous that the access to the support plate is limited for medical personnel either at the head or at the foot of the support plate due to the proximity to the gantry. Furthermore, the sole longitudinal movement capability of the support plate proves to be disadvantageous when a whole-body scan of a patient must be generated. In this case., the scan length presently available in computed tomography apparatuses is normally insufficient permit to scanning a patient without repositioning (i.e. a 180° rotation of the patient). Such a repositioning, however, significantly reduces the speed of the workflow, and it is additionally problematical that emergency patients are not able to reposition themselves. For this reason, such patients (together with the care devices connected to them) often must be first relocated to a second bed which is rotated by 180° in order to be able to subsequently position the patient again on the support plate of the patient positioning table of the computed tomography apparatus and scan the still-remaining body segment of the patient.

SUMMARY OF THE INVENTION

An object of the present invention is to provide a patient positioning table or a computed tomography apparatus with such a patient positioning table of the aforementioned type, wherein the support of the patient on the patient positioning table is simplified.

This object is achieved in accordance with the invention by a patient positioning table having a base part with a longitudinal axis and a support plate for support a patient, the support plate being displaced in the direction of the longitudinal axis of the base part relative to the base part, the support plate having a device that interacts with an acceptance device of the base part such that the support plate can be rotated relative to the base part after an acceptance of the device of the support plate in the acceptance device of the base part. This permits the support plate to be rotated, for example by 90° relative to the base part, such that for a positioning a patient on the support plate by medical personnel, this support plate is freely accessible both at the head end and at the foot end for simplified positioning of the patient.

Furthermore, in the use of such a patient positioning table in a tomography apparatus (for example a computed tomography apparatus), the support plate can be rotated in a simple manner by 180° relative to the base part such that a whole-body scan of the patient with the tomography apparatus is possible without repositioning the patient.

A patient bed that can be displaced in the longitudinal and transverse directions and can additionally be pivoted on an axis running through a base known from DE 37 14 397 C2. The entire bed can be pivoted on the base in order to be able to feed a patient borne on the patient bed to various medical apparatuses arranged around the patient bed. A rotation of only the support plate of the patient bed relative to a base part into an advantageously-determined position of the support plate relative to the base part, which position can be adopted by longitudinal displacement of the support plate relative to the base part, is not known from DE 37 14 397 C2.

In an embodiment of the invention the device of the support plate has a disc and/or a support and/or a support pin. The support pin is connected in a fixed manner with the support plate and the disc is advantageously connected in a fixed manner with the support pin. The support (which is advantageously a roller support) is, connected by an internal bushing in a fixed manner with the support pin. The support pin and the support together form a type of guide element for the longitudinal displacement of the support plate relative to the base part.

In another embodiment of the invention the acceptance device of the base part has a housing for acceptance of the device of the support plate. One side of the housing exhibits an opening in order to enable the insertion of the device of the support plate into the housing of the acceptance device.

In a further embodiment of the invention, a housing segment of the housing of the acceptance device is fashioned as a counter-support for the support of the device of the support plate, such that the outer support shell of the support can be attached to the counter-support upon insertion of the device of the support plate into the acceptance device. In order to enable rotation of the support plate relative to the base part, a first locking device with which the outer bushing of the support is fixed relative to the counter-support is provided on the housing segment of the acceptance device.

In another embodiment of the invention, at least one bolt interacting with the outer bushing of the shell is provided as the locking device. A number of such pins can be provided in order to fix the outer bushing relative to the counter-support.

In order to prevent an unintended rotation of the support plate relative to the base part during the insertion of the patient positioning table, in an embodiment of the invention a second locking device is provided that additionally enables the support plate to be fixed in a defined position relative to the base part. According to a version of the invention, this second arresting device has at least one locking pin. In a further embodiment of the invention the disc of the device of the support plate has a number of recesses (for example at 90° intervals) in which the locking pins can engage to lock the support plate relative to the base part.

According to a particularly preferred embodiment of the invention, a lifting device is associated with the acceptance device of the base part such that, after an insertion of the device of the support plate into the acceptance device of the base part, the support plate can be raised in order to enable rotation of the support plate relative to the base part in a simple manner.

If the base part has side walls, in a version of the invention the side walls of the base part can be pivoted downwardly. The rotation of the support plate relative to the base part can be enabled in this manner by a relatively small lift of the support plate relative to the base part.

The support plate can be adjustable along at least one rail. Both the longitudinal adjustment of the support plate and the rotation of the support plate relative to the base part can ensue manually and/or in a motorized manner.

Position sensors can be provided in the patient positioning table in order to detect both the position of the support plate in the direction of the longitudinal axis of the base part and the rotation angle of the support plate relative to the base part, and provide the acquired position signals to a computer for further processing.

The above object also is achieved by a computed tomography apparatus having a patient positioning table of the type described above.

DESCRIPTION OF THE DRAWINGS

FIG. 1 shows a computed tomography apparatus with a patient positioning table in accordance with the invention.

FIG. 2 shows components of the patient positioning table of FIG. 1 in an exploded view.

FIG. 3 shows the components of the patient positioning table of FIG. 2 combined with one another.

FIG. 7 shows various rotation positions of the support plate of the patient positioning table as seen from above.

DESCRIPTION OF THE PREFERRED EMBODIMENTS

Figure 4:
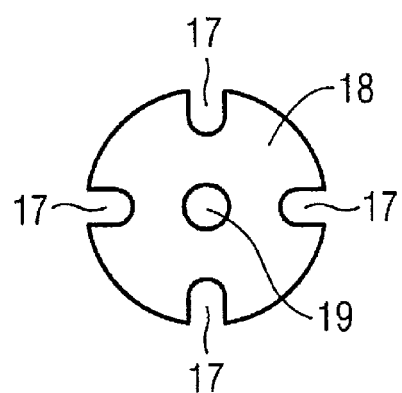
FIGS. 4 through 6 show further components of the patient positioning table of the computed tomography apparatus.

A computed tomography apparatus 1 is shown in FIG. 1 in a schematic illustration. The computed tomography apparatus 1 has a gantry 2 with a rotary frame 3 that is arranged in the gantry 2 and can be rotated around a system axis Z of the computed tomography apparatus 1. An x-ray source 4 is mounted on the rotary frame 3. From the focus F the x-ray source 4 an x-ray beam RS emanates that is shaped with diaphragms (not shown in FIG. 1 but generally known), for example in a fan-shape or pyramid-shape. In the case of the exemplary embodiment, a multi-line x-ray detector 5 is arranged opposite the x-ray source 4 on the rotary frame 3.

The computed tomography apparatus 1 furthermore has a patient positioning table 6 with a base 7, a lifting column 8, a base part 9 having a longitudinal axis L and a support plate 10. The support plate 10 can be adjusted in the direction of the longitudinal axis L of the base part 9 (this longitudinal axis L running essentially parallel to the system axis Z) on rails running essentially parallel to the longitudinal axis L. Sliding rails 11 arranged on the support plate 10 run in rail elements 12. The displacement movement can ensue manually or in a motorized fashion by means of electromotors (not shown).

For examination of a patient (not shown in the figures), this patient is positioned on the support plate 10 and this is moved with the patient into or through the opening 13 of the gantry 2. In a spiral mode under continuous table feed, x-ray radiation RS emanating from the focus F of the x-ray source 4 penetrates the patient to be examined and impinges on the x-ray detector 5. The rotary frame 3 with the x-ray source 4 and the x-ray detector 5 rotates around the system axis Z of the computed tomography apparatus 1, i.e. around the patient, so that x-ray exposures of the patient are acquired from different projection directions. In each x-ray projection, x-ray radiation passing through the patient and attenuated due to the passage through the patient strikes the x-ray detector 5. The x-ray detector generates signals corresponding to the intensity of the incident x-ray radiation. A computer 14 subsequently calculates one or more two-dimensional or three-dimensional images of the patient from the signals determined with the x-ray detector 5. These images can be shown on a viewing device (monitor) 15. Input means such as the keyboard exemplarily shown in FIG. 1 are provided for operation of the computed tomography apparatus 1.

In order to be able to more simply position a patient on the support plate 10 of the patient positioning table 6, in particular when the patient is not able to place himself or herself on the support plate 10, and in order (as discussed above) to enable whole-body scans of a patient without repositioning of the patient, the support plate 10 has a device that can interact with an acceptance device of the base part 9 such that the support plate 10 can be rotated relative to the base part 9. For this purpose, the device of the support plate 10 has a disc 18 with recesses 17. The disc 18 is shown in detail in FIG. 4. The disc 18 is fastened to the underside of the support plate 10 with a support pin 9 in a recess of the support plate 10. A roller support 20 is fastened to the support pin penetrating the disc 18 on the side facing way from the support plate 10. The inner support shell 21 of the roller support 20 is thereby connected in a fixed manner with the support pin 19. By contrast, the outer bushing 22 is free such that a rotation of the outer bushing 22 is possible.

Figure 5:
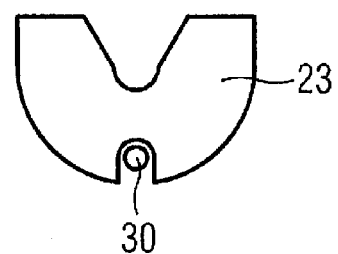
Figure 6:
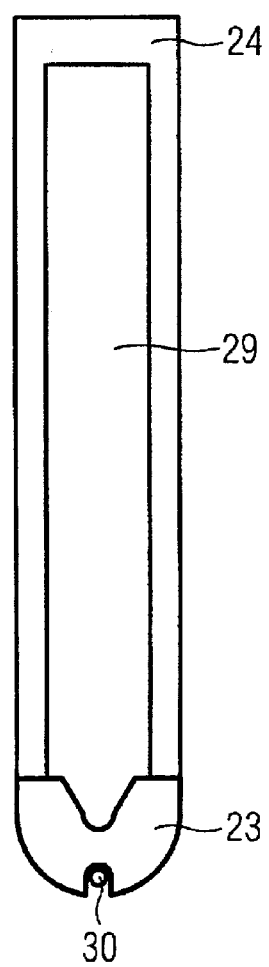

The base part 9 has a housing 23 for acceptance of the device of the support plate 10. The housing 23 has an opening on one side for this purpose and, in the exemplary embodiment, is arranged on one end of a table slide rail 24 of the base part 9. The housing 23 of the acceptance device has a housing segment 25 serving as a counter-support for the outer bushing 22 of the roller support 20 of the device of the support plate 10. The housing 23 of the acceptance device of the base part 9 is again shown as seen from above in FIG. 5, from which it is apparent that the device of the support plate 10 can be inserted into the housing 23 of the acceptance device.

When the device of the support plate 10 is inserted into the housing 23 of the acceptance device of the base part 9, the outer bushing 22 of the roller support 20 of the support plate 10 rests on the housing segment 25 (acting as a counter-support) of the housing 23 of the acceptance device of the base part 9. To secure the outer bushing 22 against rotation relative to the housing segment 25, a number of locking pins 26 are provided that can be engaged with the outer support shell for fixing purposes, but without impairing the operation of the roller support 20.

In principle, after such an insertion of the device of the support plate 10 into the housing 23 of the acceptance device, it is possible to rotate the support plate 10 relative to the base part 9 by means of the roller support 20. However, when (as in the case of the exemplary embodiment) the base part 9 has side walls 27 for stabilization of the longitudinal displacement of the support plate 10 and moreover rails 11, 12 are present for longitudinal displacement of the support plate 10 relative to the base part 9, another lifting device 28 (shown in FIGS. 2 and 3) associated with the acceptance device is present in the base part 9. The lifting device 28 allows the support plate 10 to be raised off the rails 11, 12. In the exemplary embodiment, to limit the lifting the side walls 27 of the base part 9 can be pivoted downwardly, as shown in FIG. 3, such that only a slight raising of the support plate 10 relative to the base part 9 is necessary in order to attain the necessary clearance that enables a rotation of the support plate 10 relative to the base part 9.

To make the insertion of the device of the support plate 10 into the acceptance device of the base part 9 easier, the base part 9 has the table slide rail 24 (already mentioned) that is provided with a recess serving as a guide rail 29, in which recess at least the roller support 20 runs given a longitudinal displacement of the support plate 10 relative to the base part 9. If applicable, the recess can be designed such that the disc 18 also runs in the recess.

If the support plate 10 is displaced in the negative z-direction, thus out from the opening 13 of the gantry 2, the device of the support plate 10 is inserted into the acceptance device at the fixed, selected attachment (mounting) location of the acceptance device. The outer bushing 22 is subsequently fixed with the locking pins 26 relative to the housing segment 25 of the acceptance device. Finally, the rotation of the support plate 10 relative to the base part 9 is enabled by raising the acceptance device and thus the support plate 10, as well as by the pivotable side walls 27.

In the exemplary embodiment, the disc 18 of the device of the support plate 10 has four recesses 17 that interact with a further locking pin 30 (shown in FIG. 5) of the acceptance device of the base part 9. If a specific rotation position (which, in the exemplary embodiment, can be 90°, 180°, 270° or 360°) is adopted, the respective position can be fixed by the locking pin 30 in order to prevent an unwanted further rotation of the support plate 10 relative to the base part 9.

The rotation positions of the support plate 10 relative to the base part 9 of the patient positioning table 6 that are possible in the exemplary embodiment are shown in FIG. 7.

The device of the support plate 10 is moreover advantageously arranged on the underside of the support plate 10 such that the support plate 10 is essentially supported at its center of gravity. Furthermore, the support plate 10 has table reinforcement rails 33 in order to largely prevent a deflection of the support plate 10 after raising the support plate 10.

Like the longitudinal displacement of the support plate 10, the rotation of the support plate 10 in the case of the present exemplary embodiment can also ensue manually or in a motorized fashion. One or more known electromotors M (schematically shown in FIG. 1) can be provided for this purpose. In order to be able to show a user the position of the support plate 10 (be it in the direction of the longitudinal axis of the base part 9 or with regard to its rotation) on the viewing device 15 of the computed tomography apparatus, position sensors 31 and 32 are provided that are schematically shown in FIGS. 1 and 3. The position sensors transmit position signals to the computer 14 so that these can be displayed in a suitable manner on the viewing device. The position sensors 31, 32 also enable previously-established positions of the support plate 10 to be exactly adopted by operator inputs into the computed tomography apparatus 1.

The patient positioning table 6 was described in the preceding in connection with a computed tomography apparatus 1. The patient positioning table 6 is not limited to use in or on computed tomography apparatuses. The patient positioning table also is suitable for other tomography apparatuses. Given a use of the patient positioning table in tomography apparatuses that operate with x-ray radiation, the components of the patient positioning table should be fashioned from suitable x-ray-transparent materials in order to not negatively influence the diagnostics.

Although modifications and changes may be suggested by those skilled in the art, it is the intention of the inventor to embody within the patent warranted hereon all changes and modifications as reasonably and properly come within the scope of his contribution to the art.

I claim as my invention:

1. A patient positioning table comprising:
   a base having a longitudinal axis and a vertical axis;
   a support plate disposed on said base, and being configured to receive a patient thereon, said support plate being displaceable relative to said base along said longitudinal axis;
   an acceptance device on said base; and
   a plate device attached to said support plate that projects into said acceptance device and structurally interacts with said acceptance device that allows rotation of said support plate relative to said base axis and that arrests said rotation and holds said plate device and said support plate only at a plurality of rotational positions relative to said base.

2. A patient positioning table as claimed in claim 1 wherein said plate device comprises a disk.

3. A patient positioning table as claimed in claim 2 wherein said plate device comprises a support mounted on said disk that reduces friction during rotation of said support plate relative to said base.

4. A patient positioning table as claimed in claim 1 comprising a support pin connecting said disk to an underside of said support plate.

5. A patient positioning table as claimed in claim 1 wherein said acceptance device comprises a housing in which said plate device is received.

6. A patient positioning table as claimed in claim 5 wherein said housing has an open side facing said support plate allowing insertion of said plate device into said housing.

7. A patient positioning table as claimed in claim 5 wherein said plate device comprises a friction-reducing bearing, and wherein said housing comprises a housing segment in which said bearing is received, said housing segment forming a counter-bearing in combination with said bearing, allowing said rotation of said support plate relative to said base.

8. A patient positioning table as claimed in claim 7 comprising a locking device in said housing segment that is actuatable to interact with said plate device to arrest said rotation of said support plate relative to said base at each of said rotational positions.

9. A patient positioning table as claimed in claim 8 wherein said locking device comprises a pin in said housing segment movable, upon actuation thereof, to interact with said plate device.

10. A patient positioning table as claimed in claim 8 wherein said locking device is a first locking device, and comprising a second locking device disposed in said housing segment that is actuatable to assist said first locking device in arresting said rotation of said support plate relative to said base.

11. A patient positioning table as claimed in claim 10 wherein said second locking device comprises a pin in said housing segment that is movable, upon actuation thereof, to interact with said plate device.

12. A patient positioning table as claimed in claim 11 wherein said plate device comprises a disk that is received in said housing segment, said disk having a recess in which said pin of said locking device is received to arrest said rotation of said support plate relative to said base.

13. A patient positioning table as claimed in claim 1 wherein said acceptance device comprises a lifting device operable to interact with said plate device to lift said support plate relative to said base.

14. A patient positioning table as claimed in claim 1 wherein said base comprises a bottom element, on which said acceptance device is disposed, and side walls pivotably attached to said bottom element on opposite sides of said acceptance device, and spaced from said acceptance device, said side walls each being outwardly and downwardly pivotable relative to said base bottom to free said support plate for said rotation of said support plate relative to said base.

15. A patient positioning table as claimed in claim 1 wherein said base comprises at least one rail proceeding parallel to said longitudinal axis, along which said support plate is displaced.

16. A patient positioning table as claimed in claim 1 wherein said support plate is manually displaceable relative to said base.

17. A patient positioning table as claimed in claim 1 comprising a motor mechanically coupled to said support plate to displace said support plate relative to said base.

18. A patient positioning table as claimed in claim 17 comprising a position sensor that identifies a position of said support plate relative to said base for use in controlling displacement of said support plate by said motor.

19. A patient positioning table as claimed in claim 1 wherein said support plate is manually rotatable relative to said base.

20. A patient positioning table as claimed in claim 1 comprising a motor mechanically coupled to said support plate to rotate said support plate relative to said base.

21. A patient positioning table as claimed in claim 20 comprising a position sensor that identifies a position of said support plate relative to said base for use in controlling rotation of said support plate by said motor.

22. A computed tomography apparatus comprising:
a gantry having a central opening therein;
a rotatable frame disposed for rotation in said gantry;
an x-ray source and an x-ray detector mounted on said rotatable frame for rotation with said rotatable frame around said opening; and
a patient positioning table for moving a patient into and out of said opening, said patient positioning table comprising a base having a longitudinal axis, a support plate disposed on said base and being configured to receive a patient thereon, said support plate being displaceable relative to said base along said longitudinal axis, an acceptance device on said base, and a plate device attached to said support plate that projects into said acceptance device and interacts with said acceptance device to allow rotation of said support plate relative to said base axis and that arrests said rotation and holds said plate device and said support plate only at a plurality of rotational positions relative to said base.

* * * * *